United States Patent [19]
Mueller et al.

[11] Patent Number: 5,837,235
[45] Date of Patent: Nov. 17, 1998

[54] PROCESS FOR REGENERATING BONE AND CARTILAGE

[75] Inventors: Werner Mueller, Wiesendangen; Thomas Thaler, Zürich, both of Switzerland

[73] Assignee: Sulzer Medizinaltechnik AG, Winterthur, Switzerland

[21] Appl. No.: 602,833

[22] PCT Filed: Jul. 6, 1995

[86] PCT No.: PCT/CH95/00158

§ 371 Date: May 9, 1996

§ 102(e) Date: May 9, 1996

[87] PCT Pub. No.: WO96/01641

PCT Pub. Date: Jan. 25, 1996

[30] Foreign Application Priority Data

Jul. 8, 1994 [CH] Switzerland .............................. 2190/94

[51] Int. Cl.⁶ .............................. C12N 5/06; C12N 5/08; C12N 11/02; C12N 11/08
[52] U.S. Cl. ......................... 424/93.7; 424/422; 424/520; 435/176; 435/177; 435/180; 435/395; 435/396; 435/402
[58] Field of Search ..................... 424/93.7, 520; 435/174, 176, 177, 180, 182, 240.2, 240.23, 395, 396, 402

[56] References Cited

U.S. PATENT DOCUMENTS 4,458,678  7/1984  Yannas et al. ........................... 128/155
4,609,551  9/1986  Coplan et al. ............................. 424/95
5,041,138  8/1991  Vacanti et al. ............................. 623/16

FOREIGN PATENT DOCUMENTS 0 570 331 A1  11/1993  European Pat. Off. .
WO86/01111   2/1986   WIPO .
WO 87/03812  7/1987   WIPO .

Primary Examiner—David M. Naff
Attorney, Agent, or Firm—Lowe Hauptman Gopstein Gilman & Berner

[57] ABSTRACT

Bone and cartilage are regenerated in a patient by a process of removing fatty tissue such as omentum tissue from a patient, comminuting the tissue to form small tissue particles, suspending the particles in a liquid to form a suspension, depositing the suspension on a solid carrier to prepare a solid implanting material, implanting the implanting material in a patient in an environment favoring bone or cartilage formation, and regenerating bone or cartilage in the patient. The carrier can be demineralized bone, collagen, mineral material or synthetic polymer material in pulverulent, textile, porous particle or monolith form. A cell adhesion agent may be applied to the carrier or added to the suspension, and a growth factor may be deposited on the carrier. Comminuting is performed by digesting with an enzyme and/by mechanically comminuting. Liquid used to form the suspension may contain a gel precursor which is gelled after the suspension is deposited to the carrier. Preferably, the implanting material is implanted within about 1 hour of removing the fatty tissue from the patient.

26 Claims, 1 Drawing Sheet

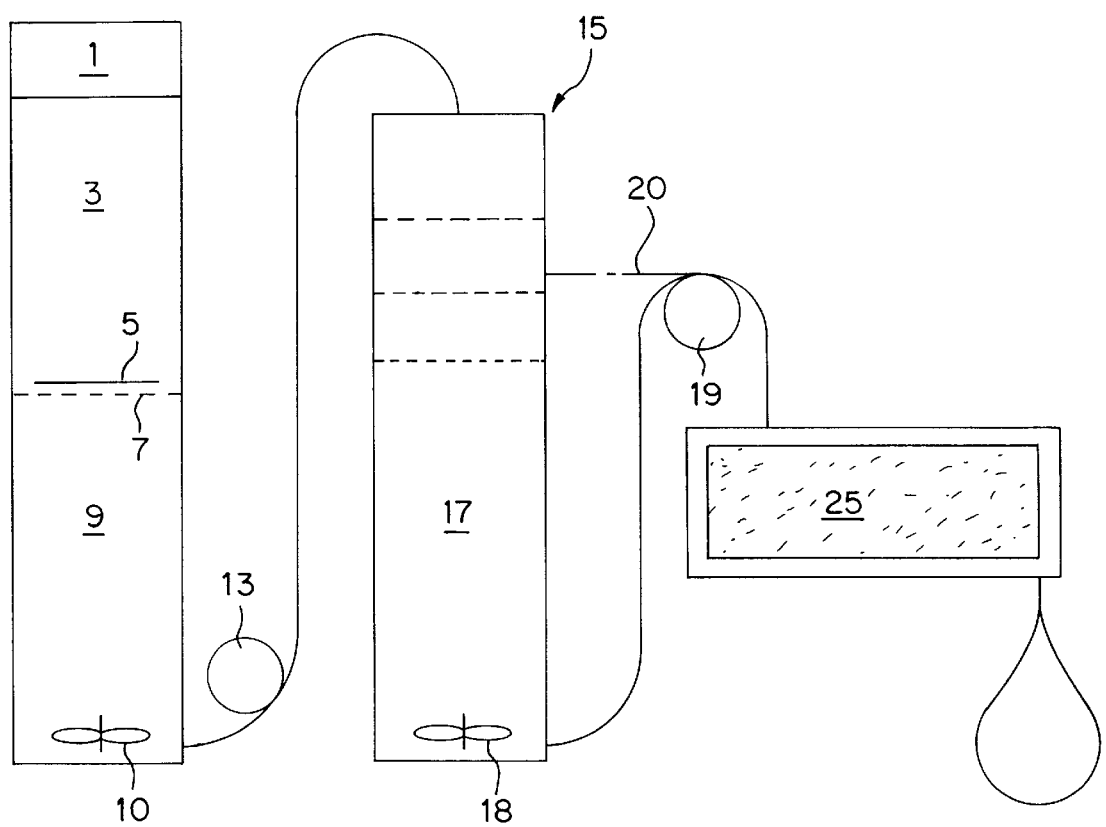

PROCESS FOR REGENERATING BONE AND CARTILAGE

This application is a 371 of PCT/CH95/00158, filed Jul. 6, 1995.

The invention relates to a process for producing implant materials with bone-regenerating and/or cartilage-regenerating characteristics.

BACKGROUND OF THE INVENTION

The healing of bone regression, such as can e.g. occur in connection with artificial prostheses, or the healing or treatment of serious bone damage caused by accidents can, according to the prior art, be brought about or improved/accelerated at the damaged points by inplantation of endogenic material, e.g. in the form of a mixture of ground bone material and blood. As a result of the vital osteoblasts present in the implanted bone material a regeneration of bone material is initiated or assisted at the damaged point. Such bone material autotransplantations are admittedly very complicated, but offer the best prospects to bring about healing and cure in very difficult cases.

The difficulties encountered in the autotransplantation of bone material are in particular that the removal of the material, e.g. from the iliac crest, represents a relatively serious operation and that the removable quantity, particularly in children is very small. As a result of these difficulties, autotransplantation of bone material as the method with the highest healing chances is only used in the most serious cases.

In order to overcome the problem of the quantitative availability of endogenic bone material, it has therefore been proposed to remove it from the patient and subsequently reproduce or propagate the osteoblasts contained therein in vitro (A. I. Caplan, J. Orthop, Res. 9, 641–650, 1991). M. J. Doherty et al. (Bone and Mineral 25, Suppl. 1, p 9, 1994) have shown on rats that in bone damage areas implanted, demineralized bone material, which was coated beforehand with in vitro propagated osteoblasts of rats, improved the healing of bone damage and in fact did so more than implanted, demineralized bone material without such a coating, which although assisting bone regeneration, can clearly not initiate the latter. The difference in the results of the two healing attempts was that when using demineralized bone material alone, there was only a bone growth from the edges of the damage, i.e. from the living, damaged bone, whereas when using coated bone material it started directly on the latter, i.e. from the centre of the damage. In many cases of treatment with only demineralized bone material radioulnar coalescence was observed, but this did not occur in the case of treatment with coated material.

Similar healing improvements were obtained by Shigeyukui Wakitani et al. (The Journal of Bone and Joint Surgery, vol. 76-A, No. 4, April 1994, pp 579 to 592), who used a collagen gel for the treatment of defects in stressed knee joint surfaces of rabbits and into said gel was incorporating endogenic cells extracted from the bone marrow or periosteum and which was cultured in vitro. It was found that the implant material in particular assisted and improved the regeneration of the joint cartilage, and also assisted in the regeneration of the underlying bone. It can be gathered from the tests described, that cells obtained from bone material (mesenchymal cells) are able to form bone or cartilage, as a function of the particular environment.

The advantage of a method in which bone material is taken from the patient, propagated in vitro and then implanted at the damaged point of a bone, compared with the direct autotransplantation method, is that there is a much larger quantity of vital material available for implantation purposes. The disadvantage is that for the removal or extraction of the material, the same difficult operation is needed, which must be separated in time from the implant operation by e.g. six weeks for in vitro culturing purposes.

SUMMARY OF THE INVENTION

The problem being addressed by this invention is to provide a process for producing an implant material with characteristics for regenerating bone and/or cartilage, with which the aforementioned disadvantages of the known methods are avoided and in particular to provide means to make it possible to obviate the seriousness of the removal operation, the low available quantity of vital material, or the time separation between the bone matter removal operation and the implant operation.

Thus, using the process according to the invention it is to be possible to produce, from endogenic material taken from the patient in an easily performable removal operation immediately preceding the implant operation, an implant material and to use it at the damaged point in an implant operation directly following the removal operation. When using the implant material produced according to the process of the invention the healing chances are significantly better than when implanting purely artificial (not-vital) materials.

The technical problem is to process a suitable endogenic material in the short time between the removal operation and the implant operation, i.e. in approximately one hour, so as to give a suitable implant material. The advantages resulting from the process according to the invention and the implant materials produced by it relate to the removal operation and the healing chances, i.e. the activity of the surgeon and the situation of the patient.

BRIEF DESCRIPTION OF THE DRAWING

The FIGURE shows an apparatus for producing implant material.

DETAILED DESCRIPTION OF THE INVENTION

According to the invention the omentum, or other fatty tissue taken from the patient, is comminuted to small particles, said tissue particles are suspended in a carrier to form a suspension, the tissue particles from the suspension are applied, e.g. by filtering, to a carrier material suitable for treating the damage and the remaining suspension is separated. Depending on the specific implantation application, the carrier material can be pulverulent or gel-like and the finished implant material can be paste-like, so that it is suitable for use in implants that have no mechanical strength function requirements, e.g. for the treatment of missing bones and/or cartillage due to regression, tumor removals, etc. However, the carrier can also be substantially preshaped and sponge-like or porous and can e.g. comprise a ceramic or metallic material and, as a function of the specific chosen carrier material, can fulfil a mechanical strength function. The aforementioned paste-like material can also be applied to a carrier material which provides the mechanical function.

The removal or extraction of omentum or other fatty tissue is a very simple operation. In addition, such tissue can be removed without harmful consequences to the patient in much larger quantities than bone material. From 1 g of fatty tissue it is possible to isolate between $50 \times 10^3$ and $200 \times 10^3$ vital cells, which is sufficient for producing approximately 1 ml of paste-like implant material or for producing a corresponding volume of a porous shaped carrier.

In addition to other cells and non-cellular tissue fractions, omentum or other fatty tissue, also contains cells suitable to form (or produce) ossified tissue and/or cartilage. This can be deduced from the existence of ectopic bone formations, which under certain circumstances can occur at body points, at which no bone marrow and no periosteum is present, these being known to contain bone tissue and cartilage-forming osteoblasts or mesenchymal cells (cf. hereinbefore). Thus, if the tissue particles applied to the carrier material are exposed to a bone or cartilage formation-favouring medium, they will initiate a bone or cartilage formation of the same type as would result from implanted, endogenic bone material with osteoblasts or mesenchymal cells cultured in vitro on a carrier material.

Frequently the environment around the point to be treated will be sufficient for producing a corresponding medium. Other means for producing a bone formation-favouring medium, such as e.g. bone matrix, hydroxyapatite, hydroxyapatite ceramic, etc. are known per se and need not therefore be described here.

In addition to the bone and/or cartilage formation-initiating cells, fatty tissue also contains endothelial cells, which, after implantation, leads to a vascularization of the bone tissue being formed, so that there is a good blood flow through said tissue and the healing and mineralization are positively influenced. In certain circumstances such endothelial cells should be removed for the regeneration of cartilage through which there is no blood flow.

The carrier for the implant materials for bone defects can be most of the per se known, non-vital bone implant materials, i.e. materials having a biological origin (demineralized bone material, collagen sponge), degradable or non-degradable, synthetic polymers, mineral materials such as hydroxyapatite or hydroxyapatite ceramic or metals and, as previously stated, part of these materials also ensure that there is a bone formation-furthering medium. For aiding mineralization, the carrier material can also be provided with growth factors, such as e.g. TGFβ (Transforming Growth Factor Beta) or BMP (Bone Morphogenetic Protein). As has already been stated, the carrier can be pulverulent and can give a pasty implant material or can be preshaped and when implanted can take over the strength function of the damaged bone or part thereof. For such functions use is more particularly made of metallic gauzes and plates, e.g. of titanium.

As implant materials for cartilage or cartilage-covered bone surfaces are suitable carriers in the form of a sponge, in the form of fibrils, in the form of textiles (woven fabric, felts, etc.) or as a gel. It is possible to use as carrier materials known materials having a biological origin (e.g. collagen) and degradable and non-degradable, synthetic polymers.

The detailed performance of the process according to the invention is based on the process for the production of endoprostheses described in European patent application 93810297.7 (publication number 570331 A1) of the same applicant. It is essentially based on the following findings:

The cells initiating a bone formation need not be isolated from the vital tissue used for the production of the implant material. Other cells and non-cellular tissue fractions do not disturb the healing process. It is merely necessary to sufficiently finely comminute the tissue to tissue particles and suspend the same and immediately treat the carrier therewith.

The tissue particles are produced by mechanical comminution of the tissue material removed and, if necessary, by a following enzymatic digestion. Through a corresponding mechanical comminution it is ensured that the resulting tissue particles have a close size distribution. The action in the case of enzymatic decomposition produces a more regular and more homogeneous product.

When using tissues with a very high fat content, which could lead to fat embolisms, it is advantageous to separate off a large proportion of the fat fraction by allowing the suspended particles to settle and separating the fatty phases from the suspension.

The byproducts resulting from enzymatic digestion need not necessarily be removed, for example by filtration from the suspension before the carrier is treated therewith. If necessary, following the incorporation of the tissue particles, the carrier can be rinsed with a rinsing solution for cleaning purposes and also oily-fatty fractions can be rinsed out. If the carrier is gel-like, the tissue particles are separated from the suspension and by counterfiltration with the gelling solution, they are received in the latter. Alternatively, the tissue particles may be added to the gel precursor and mixed prior to the final solidification of the gel.

Tissue particles with a very uniform size and a high vital cell content are obtained in that the process step of mechanical comminution and the process step of enzymatic digestion are precisely matched to one another.

Of the many known enzymes for decomposition, e.g. pancreatin, dispase, trypsin, etc., collagenase has proved to be particularly suitable during in vitro tests. As a result of its specific action the collagenase contributes to dissolving out of the tissue individual cells and also small cell combinations, without damaging to any significant extent the vitality of the cells. If the collagenase had a 100% specificity for the collagen of the extracellular matrix, it could possible bring about the decomposition of the tissue without in the slightest damaging the cells or their surface. This is an ideal picture, because it has been found that cells which over a long period (e.g. two hours) are exposed to the action of proteolytic enzymes or trypsin, suffer damage to their surface receptors and could even lose their entire vitality. These effects are much weaker or may not even be detectable in the case of suitable collagenase preparations.

Thus, the duration of the enzyme action must be sufficiently long to split off the tissue into sufficiently small particles and this time requirement is greatly dependent on the size of the particles that are available. However, it must not be too long, so as not to unnecessarily reduce the vitality of the dissolved out cells. Since, therefore, for particles of different sizes there are no common, optimum digestion parameters, it must be ensured by a corresponding mechanical comminution of the tissue, that the tissue parts to be digested have an optimum size for enzymatic digestion and are therefore preferably all of roughly the same size.

According to the invention, the enzymatic digestion is preceded by a cell-protecting, mechanical comminution, so as to produce tissue particles which are all of about the same size. Comminution processes are cell-protecting (atraumatic), if the tissue is cut and not squeezed or crushed. According to the invention this is achieved by treating the tissue with a plurality of very sharp blades moved in a coordinated manner.

A close, precisely defined size distribution of the tissue particles to be digested makes it possible to determine a clearly defined, optimized collagenase action time.

The process according to the invention consists of the following steps.

1. preparation of a suspension of tissue particles of endogenic omentum or other fatty tissue,
2. (possible) separation of excessively large tissue particles and/or most of the fatty fractions,
3. (possible) intermediate storage of the suspension,
4. application of the tissue particles to the carrier by filtering the suspension through the carrier (porous or pulverulent carrier), by filtering with the carrier (pulverulent carrier), filtering off and subsequent counterfiltration with a gelling liquid (gel-like carrier) or mixing with a not completely solidified gel (gel-like carrier),
5. (possible) rinsing of the implant material consisting of carrier material and associated tissue particles,
6. (possible) treatment of the implant material for obtaining the moisture level necessary for the applied, vital cells,
7. (possible) intermediate storage of the implant material produced.

Steps 1 and 4 are necessary, whereas the remaining steps may or may not be used, as a function of the implant material to be produced.

In order to keep the traumatization of the cells as low as possible, the removed tissue is very carefully mechanically comminuted, in that it is treated with a large number of very sharp blades which are moved in coordinated manner. The aim is to obtain a very high percentage of vital cells and at the same time a high, absolute cell yield. Despite these conditions the comminution must take place in a relatively short time, e.g. 1 to 3 minutes/100 g of tissue mass.

The size of the tissue fractions to be mechanically comminuted is limited by the size of the comminuting apparatus to be used and typical entry sizes are 3×3×2 cm, 5×5×2 cm or, expressed by weight, 20 to approximately 50 g pieces. These pieces are to be comminuted to small rods, disks or cubes with sizes of a few millimeters, preferably 1 to 3 mm. If subsequent digestion is not implemented, comminution is preferably to 0.5 to 1 mm particles.

Subsequently the mechanically comminuted tissue may be enzymatically decomposed, e.g. with collagenase, in order to at least partly free the cells from the connective tissue and consequently further comminute the tissue particles. The collagen and elastic fractions of the connective tissue are decomposed, so that the cells are freed, but damaged to a minimum extent (minimum decomposition of constituents of the cell surface). The enzymatic decomposition must also take place as rapidly and carefully as possible, which is controlled by means of the temperature and enzyme concentration. A thorough mixing of the phases is brought about by movement and this additionally speeds up decomposition.

Various such procedures for the treatment of living cells are known and can be correspondingly applied. It has surprisingly been found that stirring with a magnetic stirrer is more efficient than shaking the complete reaction vessel. The magnetic stirrer rods can appropriately be members having no sharp edges and preferably rounded rods, because they prevent a rolling up of the tissue. The stirrer is freely suspended or has only a minimum bottom contact, so that a grinding of the suspended cellular material is prevented.

It is e.g. possible to use collagenase for decomposition and a recommended concentration is approximately 400 to 20,000 Mandl-U/ml, typically 750 to 3,000 U/ml, the temperature being at least 37° C., but not exceeding 40° C. and preferably 37° to 38° C. and the tissue to enzyme solution volume ratio is 1:1 to 1:2.

Following decomposition the suspension can be separated for partial purification. This part of the process must also be rapidly performed, because the material involved has a relatively high metabolic activity under the processing temperatures, as opposed to the processing of cooled tissue materials. In addition, a rapidly performable process is sought for medical reasons. A purification of the suspension with a view to bringing about a quantitative separation of the enzymes used or the separation of cells other than those desired for bone and/or cartilage formation is, as has already been stated, unnecessary for most applications.

A partial separation of the suspension for removing excessively large particles or part of the fat-containing fractions can be advantageous. This can be performed either utilizing the specific weight (allowing the suspended particles to settle and separating the lighter phase) and/or the size of the aggregates (filtration). Both separating methods will be briefly discussed hereinafter.

Firstly specific weight-based separation (allowing the suspended particles to settle and separating the layers): in the case of fatty tissues, there is a relatively rapid upward floating of particles of the suspension which have a sufficiently large fat fraction. Contrary to the prevailing opinion there is no need for forced sedimentation by centrifuging and instead sedimentation in the gravitational field is sufficient. This leads to the advantage that sedimentation can be carried out in a closed, static system.

Sedimentation can be accelerated, e.g. by a suitable choice of the depth of the sedimentation vessel, by diluting the suspension at the end of enzymatic decomposition and/or by other appropriate measures. For example, the suspension to be sedimented is diluted with a buffer solution to 1.5 to 10 times, preferably 1.5 to 2 times the volume, e.g. 300 g of tissue+300 ml of enzyme solution=suspension for digestion (decomposition), which for sedimentation is topped up to 1000 ml (corresponding to a 1.67 times dilution). In a 15 cm high, 10 cm diameter, cylindrical vessel, sedimentation for such volumes lasts 1 to 15 and preferably 3 to 10 minutes. After this time there is a clear boundary between the aqueous and the oily phase. Sedimentation can be further assisted by slow stirring using a magnetic stirrer, because as a result the lighter constituents enclosed in the sediment can be released and because, particularly in the case of dense suspensions (collagenase:tissue=1:1), the separation of tissue particles on the basis of their specific weight is aided by additional, weak movement.

Sedimentation and separation of the resulting layers is preferably performed immediately following enzymatic digestion, preferably in the same vessel and at 20° to 40° C., but preferably at 30° to 37° C. for fatty tissue.

It can be advantageous to separate excessively large particles. To improve the cell yield and prevent clogging, in the case of larger material quantities (as from 50 g of tissue) multistage screens are recommended. Up to 300 g of tissue, e.g. 3 stages, the diameter of the screens being 4 to 6 cm and the spacing between two screens 2 to 6 cm. For the final screen a mesh size of 0.5 to 1 mm is to be chosen for maximum particle dimensions of 0.25 mm. This means that the entire mass of the fraction left behind does not increasingly burden a single screen layer, so that an increasing flow resistance is formed and in particular the screening effect is drastically modified, so that with increasing charging the size of the particles passing through decreases, so that there are considerable cellular material losses. However, in the case of multistage screens the total quantity, number and mesh size of the screens used are correspondingly distributed and the flow resistance and screening effect are much less influenced.

The screens are preferably horizontally superimposed, in order to be able to carry out filtration by gravity, which permits a more uniform screen charging and therefore a clearly defined filtration. In addition, with such an arrangement less equipment is needed, which also assists in connection with the strict sterility requirements.

However, filtration by pump transport or transfer is also possible, where essentially the same criteria must be respected. However, a pump transport has in particular the advantage that it permits filtration counter to gravity, which allows an air bubble-free liquid transfer in a simple manner, which is important for the subsequent carrier material treatment.

The pumps used are flow inducers, preferably those with 2-roll heads. It has surprisingly been found that this only causes insignificant vital cell losses. In simple manner the use of such pumps permits a controlled process, which is not merely just subject to gravity, in a closed system, which is not only clinically significant with respect to sterility, but is also important for the time-controlled performance of the process.

Dissolved components of the suspension, such as collagenase, which are used for enzymatic decomposition, and liquid components, such as oily fat from the tissue are, if only a size-based separation is carried out, subsequently removed during or after the treatment of the carrier material.

Subsequently the suspension is filtered through the pulverulent or porous and preshaped and, if necessary, correspondingly moistened carrier material. If it is a pulverulent carrier material, it can also be added to the suspension and filtered together therewith through a suitable filter or can be at least partly separated from the suspension solution by allowing it to settle. It may also be advantageous in such a case to add to the suspension a cell adhesion-aiding medium, such as e.g. fibronectin.

In the case of a gel-like carrier the suspension is filtered through a correspondingly fine filter and consequently the tissue particles are separated from the suspension solution. Immediately thereafter and in the opposite direction, a gelling liquid (e.g. cold, neutralized collagen solution) is pressed through the filter and consequently the tissue particles are taken up in the liquid, which is subsequently left to stand for gelling.

In order to satisfy the high sterility requirements of the process, the suspension must be kept in a closed system throughout the entire process, preferably including application to the carrier material and said closed system also contains the carrier. This is made possible e.g. by providing tube connections between the digestion vessel and the coating module, with which the incorporation of the cellular material in the carrier material is brought about. The liquid transfer can take place by gravity (different heights in the arrangement of the equipment) or by means of flow inducers, roller pumps or other positive displacement pumps, preferably those where the suspension only comes into contact with disposable parts. In the following example, for liquid delivery for the application of the cellular material to a carrier material, use is made of a Watson pump with 2 rolls having a silicone tube with an approximate diameter of 8 mm and which has no slip. It has been found that the number of vital cells in the suspension is not significantly reduced even by pumping five times.

In order that the cell vitality of the implant material produced is maintained up to the time of use, as the final stage of the process the cells can be specially protected up to wound closure. Thus, the vital cells are more particularly protected against drying.

Now, with the aid of the drawing, a discussion will take place of an example of a closed apparatus for performing the process according to the invention. The individual equipment components are in part those which are already commercially available. The interconnection of this equipment in accordance with the presently described, novel, compressed and surprisingly biologically effective process represents the process sequence according to the invention and consequently constitutes an apparatus for producing implant materials. The apparatus can be such that it can also be used in an operating theatre and permits the production of the implant material according to the invention in situ.

In a diagrammatically simplified manner the drawing shows a completely sealable apparatus, in which the entire process can be performed in a continuous, closed vessel and tube system. It can easily be placed on a movable or portable chassis or frame and in this way is mobile for use e.g. in the laboratory or operating theatre. The compact, closed nature naturally does not exclude feedlines for the solution, reagents and tissue to be processed. However, the closed nature of the apparatus is intended to illustrate how the strict sterility requirements can be met.

A first unit comprises the equipment for mechanical comminution, a drive 1, a conveyor 3, which is directed towards a knife/perforated plate pair 5, 7, and for the decomposition of the tissue material for freeing the cells a digestion cell 9 with a stirrer 10 for assisting decomposition and a first sedimentation. The equipment can be interlinked so that the comminuted tissue mass drops directly from the perforated plate 7 into the digestion vessel. At the end of digestion sedimentation the separation of the oily-fatty phase can also take place in said vessel. For this purpose at the start of sedimentation the vessel can be further topped up with buffer solution in order to assist separation. With the same aim, e.g. using a magnetic stirrer, it is possible to produce a slight movement of 0.1 to 1 U/sec. The suspension obtained in the first unit is transferred by a conveying means 13 into a second unit comprising a filter part 15 and a collecting vessel 17. During the conveying into the vessel 17, a slight flow is also produced in the vessel 9. The filter part 15 here is a multistage filter for extracting particles of a specific size and collecting the remainder as a suspension in the collecting vessel. In this form the sedimentation tendency of the suspension is only small and is eliminated in the vessel 17 by a second magnetic stirrer 18. A further conveying means 19 transfers the now usable homogeneous suspension into the third unit 25 for filter deposition on to the carrier material. This unit comprises a container, into which the e.g. pulverulent carrier material is introduced in such a way that there is a uniform flow of the entering suspension through it. Prior to the filtering of the suspension, it may be advantageous to condition the dry carrier material with physiological solution.

A pulverulent carrier material can also be supplied to the vessel 17, filtered by a filter integrated into the unit 25 or directly removed from the vessel 17.

The filter 15 can be connected, even without the vessel 17, between the vessel 9 and the unit 25 for the treatment of the carrier material, so that the suspension can be passed from the filter, without intermediate storage, directly to the carrier material. In the case of a gel-like carrier produced by gelling a liquid, in which the tissue particles are received, into the vessel 17 is placed at least one filter which is sufficiently fine for the filtration removal from the suspension of the tissue particles desired for the implant material. The filtrate is removed after filtration and a gelling liquid is pumped in the opposite direction through the filter. By means of the filter the gelling solution with the tissue particles received therein is removed from the vessel (line 20 indicated in dot-dash line) and passed into the vessel 25, which in this case serves as a gelling vessel, where it is gelled e.g. under corresponding heating.

As a function of the size and complication of the overall apparatus, it can be equipped for mass production of implant materials or for the ad hoc production of individual portions of such materials in the operating theatre.

We claim:

1. A process for the forming and applying an implant material with bone regenerating characteristics to form bone in a patient, comprising:

removing fatty tissue containing no osteoblasts or mesanchymal cells derived from bone, bone marrow or periosteum from a patient in need of bone regeneration;

comminuting said fatty tissue material to produce small fatty tissue particles;

suspending at least some of the small fatty tissue particles in a physiologically acceptable, liquid to form a suspension comprising the particles;

depositing at least a substantial portion of the suspended fatty tissue particles from said suspension on a physiologically acceptable, solid carrier material by contacting the suspension with the carrier material to form a solid implanting material;

implanting said solid implanting material into a bone in need of regeneration in a patient; and allowing bone to regenerate in the patient, wherein said removing of said fatty tissue and implanting of said implanting material are carried out in at most about 1 hour of elapsed time.

2. The process as claimed in claim 1 wherein said fatty tissue is not cultured between removal thereof from said patient and implantation thereof into said patient.

3. The process as claimed in claim 1 further wherein said solid carrier material is pulverulent.

4. The process as claimed in claim 1 wherein said solid carrier material has a form selected from the group consisting of sponge form, textile form, porous particle form, and monolith form.

5. The process as claimed in claim 1 further comprising filtering said suspension through said solid carrier material to deposit at least a substantial portion of said particles on said carrier material.

6. The process as claimed in claim 1 further comprising applying a cell adhesion agent to said solid carrier material prior to completion of contact thereof with said suspension.

7. The process as claimed in claim 1 further comprising admixing a cell adhesion agent with said suspension prior to contacting said suspension with said carrier material.

8. The process as claimed in claim 1 wherein said suspending liquid comprises a gel precursor, and said gel precursor is gelled after said tissue particles are deposited on said carrier material.

9. The process as claimed in claim 1 further comprising mechanically comminuting said fat tissue.

10. The process as claimed in claim 1 further comprising comminuting said tissue by digesting said fatty tissue with at least one enzyme.

11. The process as claimed in claim 9 further comprising, in addition to said mechanical comminution, comminuting said fatty tissue by digesting said fatty tissue with at least one enzyme.

12. The process as claimed in claim 1 wherein said solid carrier material comprises at least one material selected from the group consisting of demineralized bone, collagen, mineral material, and synthetic polymer material.

13. The process as claimed in claim 11 further comprising depositing at least one growth factor on said carrier material with said fatty tissue particles deposited thereon.

14. A process for forming and applying an implant material with cartilage regenerating characteristics to form cartilage in a patient, comprising:

removing fatty tissue material containing no chondrocytes or other cartilage forming cells derived from cartilage, bone marrow or periosteum from a patient in need of cartilage regeneration;

comminuting said fatty tissue to produce small fatty tissue particles;

suspending at least some of said small fatty tissue particles in a physiologically acceptable, liquid to form a suspension comprising the fatty tissue particles;

depositing at least a substantial portion of said fatty tissue particles from said suspension on a physiologically acceptable, solid carrier, by contacting the suspension with the carrier material to form a solid implanting material;

implanting said solid implanting material into a cartilage in need of regeneration in a patient; and allowing cartilage to regenerate in the patient;

wherein said removing of the fatty tissue and implanting of said implanting material are carried out collectively in at most about 1 hour.

15. The process as claimed in claim 14 wherein said fatty tissue is not cultured between removal thereof from said patient and implantation thereof into said patient.

16. The process as claimed in claim 14 wherein said solid carrier material is pulverulent.

17. The process as claimed in claim 14 wherein said solid carrier material has a form selected from the group consisting of sponge form, textile form, porous particles, and monolith form.

18. The process as claimed in claim 14 comprising filtering said suspension through said solid carrier material to deposit at least a substantial portion of said fatty tissue particles on the carrier material.

19. The process as claimed in claim 14 further comprising applying a cell adhesion agent to said solid carrier material prior to completion of contact thereof with said suspension.

20. The process as claimed in claim 14 further comprising admixing a cell adhesion agent with said suspension prior to contacting said suspension with said carrier material.

21. The process as claimed in claim 14 wherein said suspending liquid comprises a gel precursor, and said gel precursor is gelled after the fatty tissue particles are deposited on the carrier material.

22. The process as claimed in claim 14 further comprising mechanically comminuting said fatty tissue.

23. The process as claimed in claim 14 further comprising comminuting said tissue by digesting said fatty tissue with at least one enzyme.

24. The process as claimed in claim 22 further comprising, in addition to said mechanical comminution, comminuting said tissue by digesting said fatty tissue with at least one enzyme.

25. The process as claimed in claim 14 wherein said solid carrier material comprises at least one material selected from the group consisting of demineralized bone, collagen, mineral material, and synthetic polymer.

26. The process as claimed in claim 14 further comprising depositing at least one growth factor on said carrier material with said fatty tissue particles deposited thereon.

* * * * *